United States Patent
Kehayias

(10) Patent No.: US 6,249,564 B1
(45) Date of Patent: Jun. 19, 2001

(54) METHOD AND SYSTEM FOR BODY COMPOSITION ANALYSIS USING X-RAY ATTENUATION

(75) Inventor: Joseph J. Kehayias, Chestnut Hill, MA (US)

(73) Assignee: Trustees of Tufts College, Medford, MA (US)

( * ) Notice: Subject to any disclaimer, the term of this patent is extended or adjusted under 35 U.S.C. 154(b) by 0 days.

(21) Appl. No.: 09/272,108

(22) Filed: Mar. 19, 1999

(51) Int. Cl.[7] ................................................. G01N 23/06
(52) U.S. Cl. ................................ 378/53; 378/54; 378/37
(58) Field of Search ................................ 378/37, 53, 54

(56) References Cited

U.S. PATENT DOCUMENTS

| | | | |
|---|---|---|---|
| Re. 33,634 | * | 7/1991 | Yanaki ................................ 378/110 |
| 4,090,084 | * | 5/1978 | Epstein et al. ........................ 378/37 |
| 4,097,997 | * | 7/1978 | Bjornson .............................. 33/1 SD |
| 5,335,257 | * | 8/1994 | Stunberg ............................... 378/37 |
| 5,459,769 | * | 10/1995 | Brown ..................................... 378/4 |
| 5,526,394 | * | 6/1996 | Siczek et al. ......................... 378/37 |
| 5,715,820 | * | 2/1998 | Stein et al. .......................... 600/407 |
| 6,151,379 | * | 11/2000 | Kullenberg et al. ................... 378/54 |

OTHER PUBLICATIONS

Ken Carr–Brion. X–ray Analysers in Process Control (New York: Elsevier, 1989), p. 8–12.*

B. D. Cullity. Elements of X–ray Diffraction, second edition (Reading, MA: Addison–Wesley, 1978), p. 509–510.*

Huber et al. Nuclear Instruments and Methods in Physics Research B 99, 665 (1995).*

R.B. Mazess, et al., "Total Body Bone Mineral and Lean Body Mass by Dual–Photon Absorptiometry," *Calcif. Tissue Int. 33*, pp. 361–363 (1981).

"X–Ray and Gamma Ray Detector High Resolution CZT Cadmium Zinc Telluride," *AMPTEK, Inc.*, 6 De Angelo Drive, Bedford, Ma 01730–2204 (Advertisement).

R.B. Mazess, et al., "Dual–Energy X–Ray Absorptiometry for Total–Body and Regional Bone–Mineral and Soft–Tissue Composition," *Am J Clin Nutr 51*, pp. 1106–1112 (1990).

* cited by examiner

*Primary Examiner*—Robert H. Kim
*Assistant Examiner*—Allen C. Ho
(74) *Attorney, Agent, or Firm*—Hamilton, Brook, Smith & Reynolds, P.C.

(57) ABSTRACT

A body composition measurement device and method, particularly for soft tissue, are useful to determine levels of hydration or percent body fat, for example. It relies on the X-ray absorption analysis for a single energy or two or more energies. If only a single energy is used, then the length of the x-ray path through the soft tissue of the patient is measured. In one embodiment, body composition measurement device comprises measurement calipers, with the x-ray source and detector located on each caliper arm. The calipers determine the path length. As such, a controller either in the calipers or external to it can combine the information from the calipers and the detector to provide an indication of the body's soft tissue composition along the path.

11 Claims, 5 Drawing Sheets

METHOD AND SYSTEM FOR BODY COMPOSITION ANALYSIS USING X-RAY ATTENUATION

GOVERNMENT SUPPORT

This invention was made with government support under Contract No. 53-1950-5-003 from United States Department of Agriculture. The Government has certain rights in this invention.

BACKGROUND OF THE INVENTION

Dual photon (or x-ray) energy absorptionmetry projection techniques—also referred to as DPA, DPX or DEXA—have been used for the measurement of bone mineral density and total body composition in patients. Most commonly, total body bone mineral is calculated with full body scans to measure the effects of osteoporosis, for example. Although DEXA enables some level of soft tissue discrimination, the photon energies used are generally too high for doing non mineralogical types of body analysis.

SUMMARY OF THE INVENTION

The problem with existing techniques is the fact that they are not well suited to perform soft tissue, body composition measurements outside the laboratory environment. The systems generally require large scanning beds for total body analysis.

They also employ x-rays of high enough energy to be able to penetrate even the thickest bone in the body. This requirement seriously compromises their ability to analyze soft tissue, because the photon energies used are too high to discriminate well between fat and fat-free soft tissue.

The present invention is directed to a body composition measurement device and method, particularly for soft tissue. As such, it is useful to determine levels of hydration or percent body fat, for example. It relies on the X-ray absorption analysis at a single energy or two or more energies. If only a single energy is used, then it is preferred to measure the length of the x-ray path through the soft tissue of the patient.

In contrast to the prior art, analysis is not performed for the whole body in a total body scan or even a partial body scan. Instead, path length attenuation at only a few discrete locations is taken. Moreover, these locations are selected to avoid any bone along the path. The information on the X-ray absorption is then used to determine the body composition along the path.

Also, in contrast to the conventional approaches, with the present invention, the photon energies used are selected to be low enough to allow good soft tissue analysis, not bone.

In general, according to another aspect, the invention also features a body composition measurement device. This device comprises anthropometry measurement calipers. This can be any appropriate device for measuring the thickness of a skin fold, but large enough to measure the total thickness of a thigh or upper arm. An X-ray source is provided that emits radiation along a measurement path of the calipers and an X-ray detector is used to measure the levels of irradiation that have passed along the path. As a result, this device is most applicable to measurement at only a single energy. The calipers determine the path length. As such, a controller either in the calipers or external to it can combine the information from the calipers and the detector to provide an indication of the body composition along the path.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the drawings, like reference characters refer to the same parts throughout the different views. The drawings are not necessarily to scale, emphasis instead being placed upon illustrating the principles of the invention. Of the drawings.

DETAILED DESCRIPTION OF THE INVENTION

Figure 1:
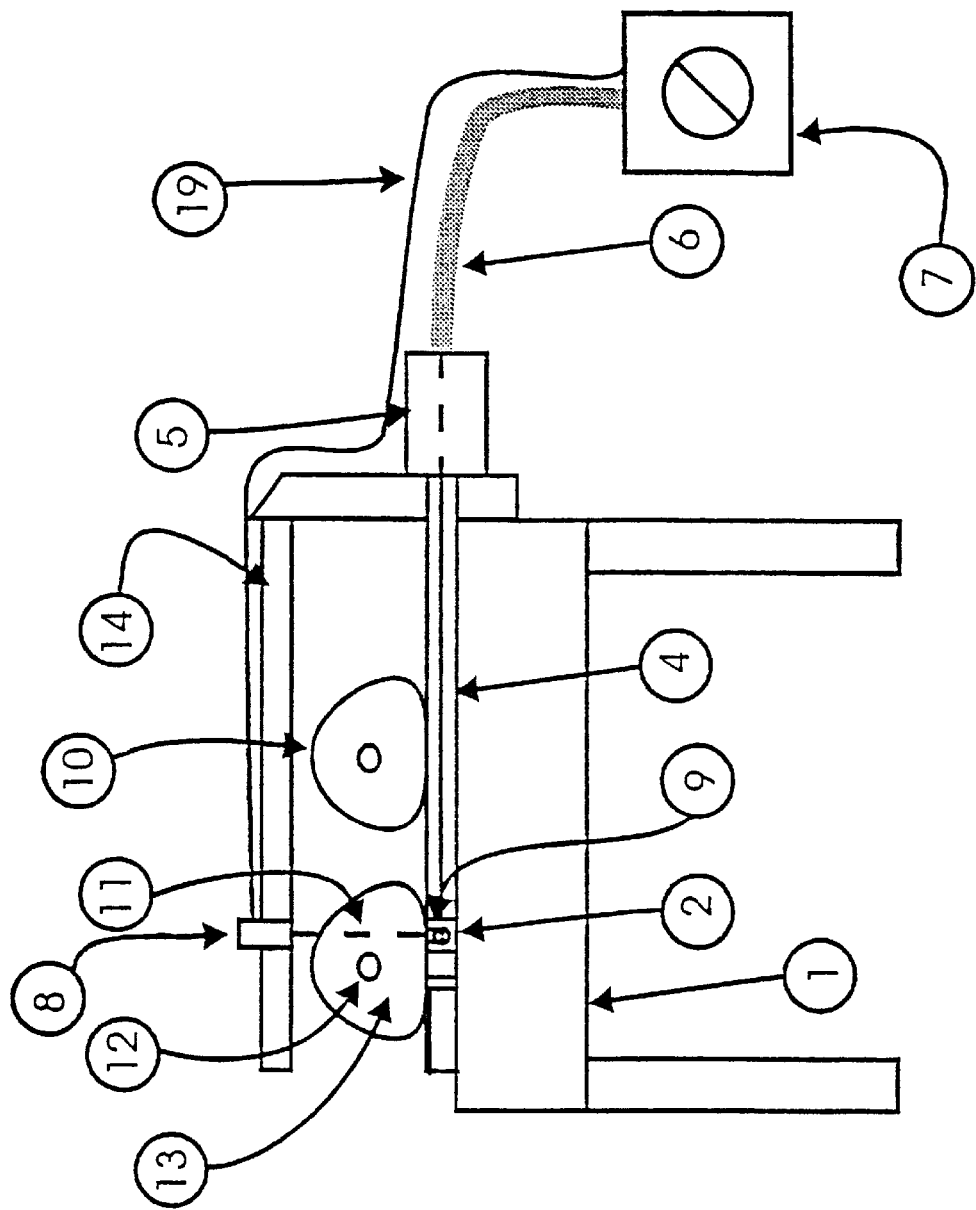
FIG. 1 is a side plan view of a first embodiment of a body composition measure device according to the present invention.

FIG. 1 shows a body composition measure device which has been constructed according to the principles of the present invention.

As illustrated, a patient reclines on a bed 1 of the instrument 100. A radioactive source 2 with a collimator 9 is placed below the thighs, for example, of the patient.

The invention is applicable either to isotope sources or X-ray tube sources. In the preferred embodiment, the source 2 emits radiation between 20 and 100 keV in energy. Appropriate sources are I-125, which emits at 21, 27, 31, and 35 keV and Am-241, which emits at 60 keV.

The source 2 emits the radiation to pass through the soft tissue 13 of the patient along a path 11. This path is selected so that the X-rays passing from the source to the detector do not encounter any hard tissue such as the femur 12. Specifically, the path should include only soft tissue.

The device can also be used in a single-line scanning mode, with the source and the detector moving together across the patient's thigh as shown in FIG. 1. In this case, bone is recognized by its large photon absorption power and is eliminated from the soft tissue analysis.

The X-rays having traversed the path 11 are received on a detector 8, which is located above the patient on an arm 14. In the preferred embodiment, the detector is a high-performance X-ray detector with integrated preamplifier and cooler system. Currently, a cadmium zinc telluride (CZT) detector mounted on a thermo-electric cooler is used. The levels of detected X-rays are sent to a controller 7.

In the preferred embodiment, the system 100 is capable of at least limited scanning. As illustrated in the current embodiment, the source 2 and collimator 9 are movable to be translated transversely to the axis of the patient's thigh 10. This is accomplished by a cable wire drive 4 that passes to a step motor 5 which is also under control of the controller 7 via cable 6. Movement along the patient axis is accomplished by moving frame 19 as one unit.

As illustrated, in the preferred embodiment, the device 100 is capable of only a line scan.

The controller 7 determines the soft tissue composition along the paths of the scan by measuring the relative attenuations at at least two separate X-ray energies. Generally, the controller 7 determines the level of beam hardening and relates this to known attenuation of X-rays in soft tissues.

Figure 2:
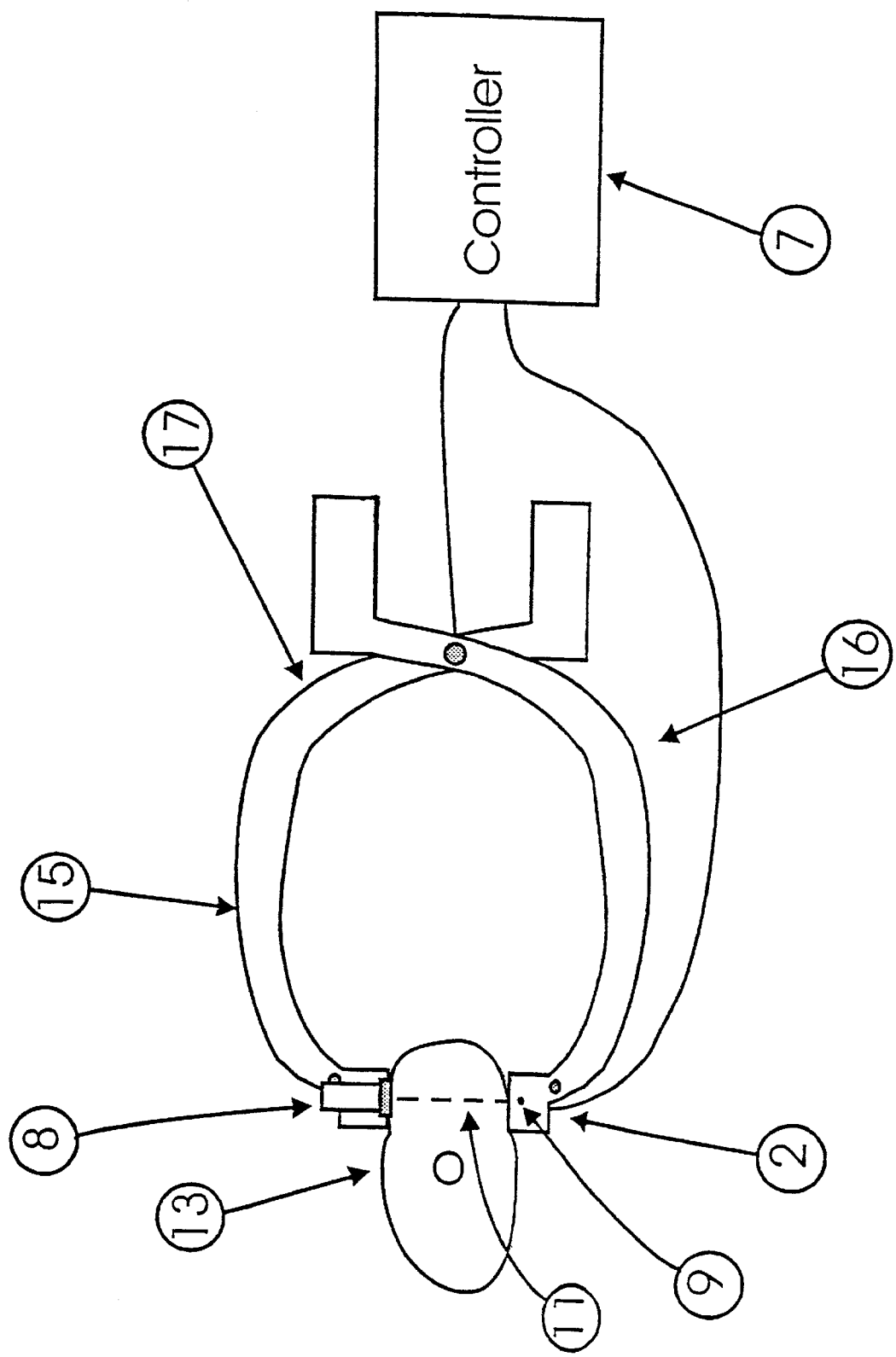
FIG. 2 is a side plan view of a second embodiment of a body composition measure device according to the invention.

FIG. 2 shows another embodiment of the body composition measuring device, which has also been constructed according to the principles of the present invention. This is a more portable system than that shown in FIG. 1.

Specifically, the detector 8 and source 2/collimator 9 are integrated at the ends of separate arms 15, 16 of skin fold measurement calipers 17. During operation, both arms 15,16 of the skin fold calipers 17 are brought into contact with the skin 13 of the patient. The calipers 17 have either a mechanical or electronic readout for determining the distance between the ends of the two arms, 15, 16, and thus, the thickness of the fold 13. Also, an encoder or similar electronic device is used that allows the controller 7 to electronically determine the distance between the two ends of the arms 15,16.

In the preferred embodiment, the detector 8 and source 2 are located on the ends of the caliber arms. This is not strictly necessary, however. The important functionality is that they measure the absorption for the path 11 for which the calipers have measured the length.

The X-ray source comprises a shutter for controlling X-ray exposure when an isotope is used to generate the x-rays.

The advantage of this system is its compactness. Body composition at different locations can be performed simply by moving the calipers to a different location on the patient. Further, absorption at only a single radiation energy is necessary since the calipers measure the path length through the soft tissue.

Figure 3:
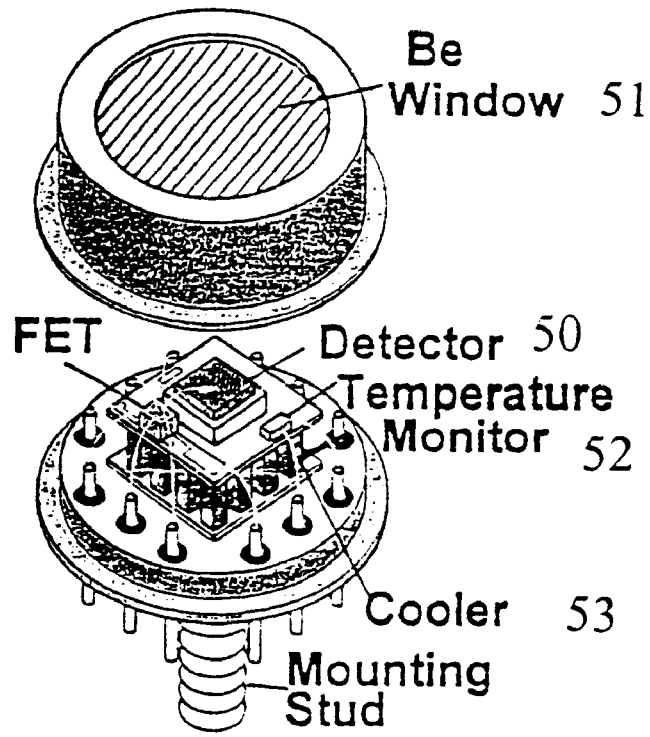
FIG. 3 is a perspective view of a compact detector to be used in the inventive body composition measure devices.

FIG. 3 shows the current implementation of the detector. This is a new high performance-type X-ray detector under current technology that has a detector element 50 located below a beryllium window 51. It further has an integral temperature monitor 52. Its innovation is an integral cooler 53, which is a thermal-electric cooler such as one working on the Peltier effect. As a result, the detector is much smaller than in the past, making it applicable to low cost, compact precision devices, such as that illustrated in FIG. 2.

Experimental Data

A collimated I-125 source was used to test the design of the two prototype assemblies.

Prototype one

A cadmium zinc telluride (CZT) detector was used to record spectral photon absorption data from the I-125 x-ray beam after its transmission through a series of phantoms, simulating different proportions of fat and lean.

Figure 4:
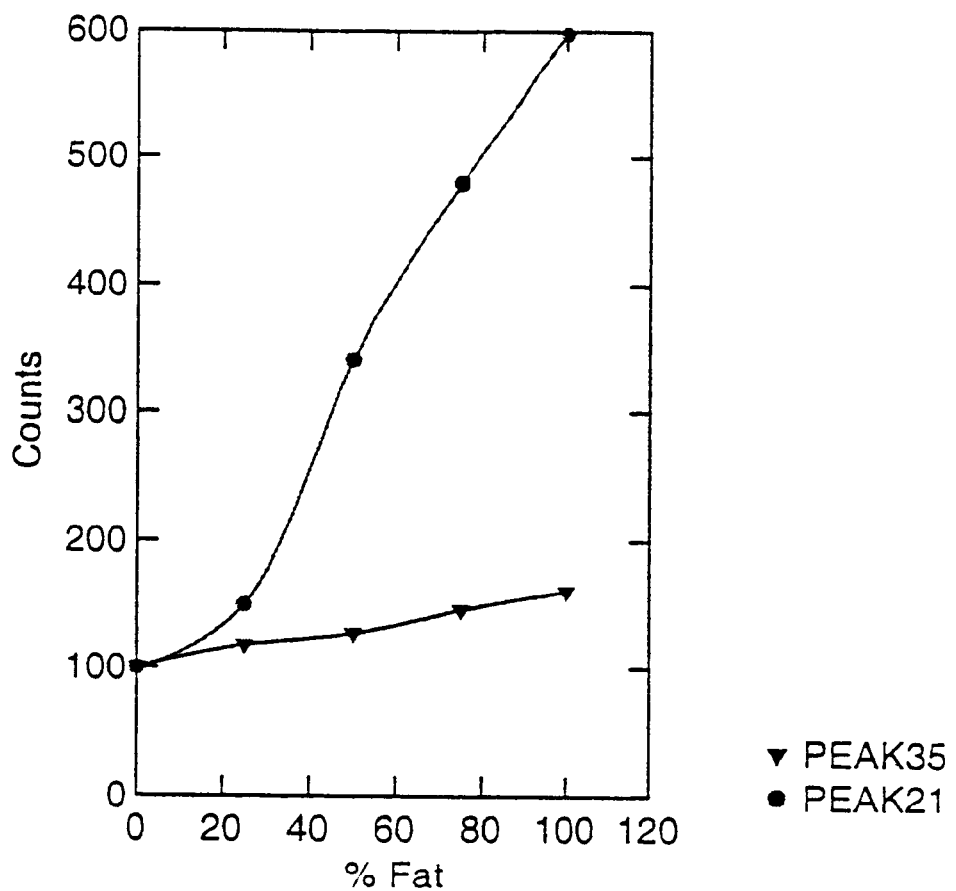
FIG. 4 is a plot of spectral photon absorption data from the I-125 x-ray beam, 21 keV (● data points) and 35 keV (▼ data points), after its transmission through a series of phantoms, simulating different proportions of fat and lean.

FIG. 4 shows two curves, which illustrate the results of the experiment for the two extreme photon energies emitted by the source: 21 and 35 keV in the embodiment described with reference to FIG. 1. The curves are presented calibrated to the point of 0% fat and demonstrate the dependence of the absorption on energy (comparison between curves) and on %fat.

Higher energies, such as the 60 keV emission of Am-241, will be less dependent on %fat and will serve as the "high energy" of the dual energy analysis method, or simply as a method for measuring thickness of lean tissue.

Prototype two

A simplified version of the device involves a separate method for measuring thickness of tissue, such as a mechanical caliper as discussed with reference to FIG. 2. When the thickness of tissue is known, the counting rate of the transmission of low energy photons derives tissue composition.

Figure 5:
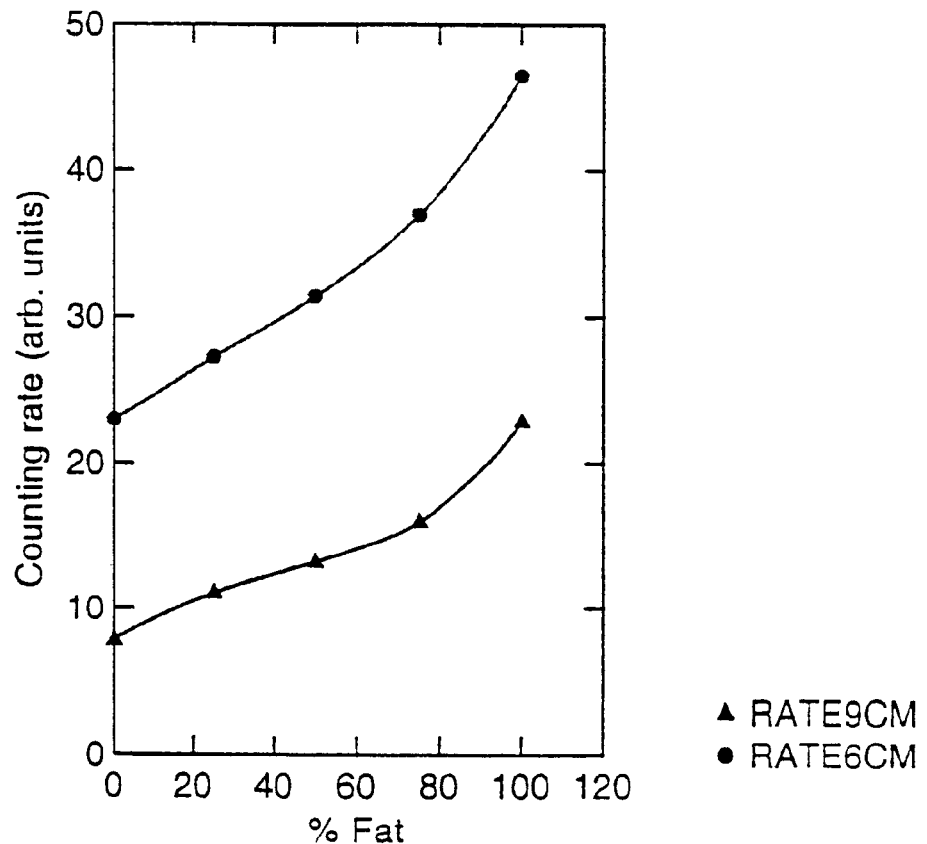
FIG. 5 is a plot of spectral photon absorption data from a low intensity I-125 collimated source and a thin (~1 mm) NaI detector using two phantom size thicknesses: 6 cm (● data points) and 9 cm (▲ data points) thick.

In FIG. 5, a prototype was put together with a low intensity I-125 collimated source and a thin (~1 mm) NaI detector. Two phantom sizes (6 and 9 cm thick) were used at several %fat values. The thickness of the NaI allowed for the collective acquisition of all photon energies emitted by the I-125 source, without high-energy background interference. As a result, no pulse-height analysis was necessary and each counting-rate data point took only 5 seconds to acquire at a reproducibility of 1%. The tissue thickness measurement, however, is required and is preferably taken by caliber or by absorption from a second, higher energy, radioactive source.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method for determining body composition, comprising:
    determining X-ray attenuation along a path through soft tissue of a patient with at least one energy, wherein the path extends from an X-ray source to a non-imaging X-ray detector;
    measuring a path length of the X-rays along the path through the soft tissue of the patient; and
    calculating a composition of the soft tissue by reference to the path length and the attenuation.

2. A method as described in claim 1, wherein the X-ray attenuation at substantially only one energy is measured.

3. A method as described in claim 1, further comprising determining the X-ray attenuation along at least two paths through different portions of the body of the patient.

4. A method as described in claim 1, wherein the X-rays are less than 100 keV and greater than 20 keV.

5. A method as described in claim 1, wherein a level of hydration is determined for the body.

6. A body composition measurement device, comprising:
- a thickness measuring device for measuring a path length along a measurement path, the measuring device having a first end and a second end;
- an X-ray source located substantially near the first end of the thickness measuring device that emits radiation with one energy along the measurement path of the thickness measuring device through the soft tissue of the patient, and
- a non-imaging X-ray detector located substantially near the second end of the thickness measuring device that measures radiation that has attenuated along the measurement path of the thickness measuring device;
- wherein the measurement path extends form the X-ray source to the X-ray detector, and the composition of the soft tissue is calculated by reference to the path length of the measurement path and the attenuation of the one energy.

7. A device as described in claim 6, further comprising a collimator for the X-ray source.

8. A device as described in claim 6, wherein the detector comprises a thermoelectirc cooler.

9. A device as described in claim 6, wherein the X-ray source is attached to one arm of the thickness measuring device and the X-ray detector is attached to another arm of the thickness measuring device.

10. A device as described in claim 6, wherein the X-ray source is an isotope.

11. A device as described in claim 6, wherein the X-ray source comprises a shutter for controlling X-ray exposures.

* * * * *

UNITED STATES PATENT AND TRADEMARK OFFICE
CERTIFICATE OF CORRECTION

PATENT NO.   : 6,249,564 B1
DATED        : June 19, 2001
INVENTOR(S)  : Joseph J. Kehayias It is certified that error appears in the above-identified patent and that said Letters Patent is hereby corrected as shown below:

Figure 1 should indicate the label 100 located above the drawing and underlined.

Signed and Sealed this

Eleventh Day of December, 2001

Attest:

NICHOLAS P. GODICI
*Attesting Officer*        *Acting Director of the United States Patent and Trademark Office*